(12) United States Patent
Ulbrich et al.

(10) Patent No.: US 10,345,202 B2
(45) Date of Patent: Jul. 9, 2019

(54) FIXING TISSUE SAMPLES USING NITROGEN-CONTAINING COMPOUNDS THAT RELEASE ALDEHYDES

(71) Applicant: Leica Biosystems Nussloch GmbH, Nussloch (DE)

(72) Inventors: Hermann Ulbrich, Bad Schönborn (DE); Markus Berberich, Heidelberg (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 102 days.

(21) Appl. No.: 14/532,252

(22) Filed: Nov. 4, 2014

(65) Prior Publication Data

US 2015/0140601 A1 May 21, 2015

(30) Foreign Application Priority Data

Nov. 15, 2013 (DE) .................. 10 2013 223 384

(51) Int. Cl.
*B01L 99/00* (2010.01)
*G01N 1/31* (2006.01)
*G01N 1/36* (2006.01)

(52) U.S. Cl.
CPC ........ *G01N 1/31* (2013.01); *G01N 1/36* (2013.01)

(58) Field of Classification Search
CPC .............. B32B 5/02; G01N 1/36; G01N 1/31; G05D 21/02
USPC ........................................ 422/536; 700/266
See application file for complete search history.

(56) References Cited

U.S. PATENT DOCUMENTS

| 4,603,115 | A | * | 7/1986 | Schweighardt | .... B01D 11/0207 210/651 |
| 5,354,370 | A | * | 10/1994 | Schmehl | .................. G01N 1/31 118/421 |
| 7,273,587 | B1 | * | 9/2007 | Birkner | .................... G01N 1/31 422/536 |
| 7,915,007 | B2 | | 3/2011 | Szabados et al. | |
| 2005/0269315 | A1 | | 12/2005 | Visinoni | |
| 2007/0243626 | A1 | | 10/2007 | Windeyer et al. | |

(Continued)

FOREIGN PATENT DOCUMENTS

| CA | 2865584 A1 | 9/2013 |
| CN | 101084746 A | 12/2007 |

(Continued)

*Primary Examiner* — Natalia Levkovich
(74) *Attorney, Agent, or Firm* — Hodgson Russ LLP

(57) ABSTRACT

A method (100) for fixing at least one tissue sample (1) is carried out using a tissue processor (10). The tissue sample (1) is introduced at a first temperature level and a first pressure level into a fixing reagent (2) containing at least one nitrogen-containing compound capable of pressure- and/or temperature-dependent release of at least one aldehyde. The tissue sample (1) is left in the fixing reagent (2) for a fixing time period during which the fixing reagent (2) is brought to a second temperature level above the first temperature level and/or to a second pressure level above the first pressure level. A concentration in the fixing reagent (2) of the nitrogen-containing compound is ascertained using at least one concentration measuring device (14) of the tissue processor (10), and a signal is outputted on the basis of a measured value of the at least one concentration measuring device (14).

3 Claims, 2 Drawing Sheets

(56) References Cited

U.S. PATENT DOCUMENTS

| | | | |
|---|---|---|---|
| 2008/0057536 A1 | 3/2008 | Szabados et al. | |
| 2011/0041599 A1* | 2/2011 | Herrmann | G01N 1/31 |
| | | | 73/290 R |
| 2012/0270193 A1 | 10/2012 | Piercey | |

FOREIGN PATENT DOCUMENTS

| | | |
|---|---|---|
| CN | 101657711 A | 2/2010 |
| DE | 3635599 A1 | 4/1988 |
| GB | 2472891 A | 2/2011 |

\* cited by examiner

FIXING TISSUE SAMPLES USING NITROGEN-CONTAINING COMPOUNDS THAT RELEASE ALDEHYDES

CROSS REFERENCE TO RELATED APPLICATIONS

This application claims priority of German patent application number 10 2013 223 384.1 filed Nov. 15, 2013, the entire disclosure of which is incorporated by reference herein.

FIELD OF THE INVENTION

The present invention relates to a method for fixing tissue samples and to a tissue processor for carrying out the method.

BACKGROUND OF THE INVENTION

Methods for fixing tissue samples using aqueous formaldehyde solutions have been known for some time.

A saturated aqueous formaldehyde solution having 37 percent formaldehyde by weight, or 40 percent formaldehyde by volume, is also referred to as "formalin." Indications as to the concentration of formaldehyde solutions that are used for fixing tissue samples typically refer to this. For example, a "ten-percent formalin" solution contains 4 percent formaldehyde by volume.

In aqueous solution formaldehyde quickly hydrates to methylene glycol, which in turn reacts with macromolecules such as proteins and glycoproteins in the tissue being fixed. What occurs firstly is the formation, on suitable amine, amide, and reactive alcohol groups among others, of hydroxymethyl groups. Only with longer fixing times do these become crosslinked to an appreciable extent.

Formaldehyde also reacts with proteins in the cell nucleus, thereby stabilizing the protein sheath of the nucleic acids. The free amino groups of the nucleic acids themselves can also react with formaldehyde, as can double bonds and thiol groups in unsaturated fatty acids. Pure carbohydrates, on the other hand, generally do not react with formaldehyde.

The reactive groups of peptides and proteins that react most intensively with methylene glycol, and thus respond best to formaldehyde fixing, are the amine groups of lysine, cysteine, histidine, arginine, and tyrosine, and the hydroxyl groups of serine and threonine. So-called "over-fixing" (tanning) results in crosslinking of lysine and of the amides of the protein backbone. Such reactions seldom occur because of the shorter fixing times typically used nowadays.

Formaldehyde has good fixing properties, but is highly hazardous to health and, upon exposure, can cause allergies and irritation of the skin, respiratory tract, and eyes. Formaldehyde is furthermore regarded as carcinogenic. Efforts are therefore being made to replace formaldehyde with less harmful compounds for the fixing of tissue samples. The same is also true of other fixing agents such as glutaraldehyde and osmium tetroxide.

In this connection it is possible to use compounds that release suitable aldehydes, especially formaldehyde. One example thereof is urotropin. The use of such compounds is known, for example, from EP 1 895 287 B1 (DE 10 2006 040 315 B4, U.S. Pat. No. 7,915,007 B2). They are also referred to as "releasers" or "donors" of the respective aldehydes.

The use of aldehyde-releasing compounds is disadvantageous in that in an equilibrium reaction they normally release only that quantity of aldehyde which is consumed by the reaction with the tissue sample. The fixing speed is therefore relatively slow as compared with conventional formalin solutions in which formaldehyde, or its hydration product methylene glycol, is present to excess. Fixing methods using corresponding donors therefore present disadvantages despite the simpler utilization and the reduced health hazard.

A need therefore exists for improved, in particular accelerated capabilities for fixing tissue samples using compounds that release aldehydes.

SUMMARY OF THE INVENTION

In light of the above, the present invention proposes a method for fixing tissue samples and a tissue processor having the features described herein. Preferred embodiments are discussed below.

Prior to an explanation of the features and advantages of the present invention, its principles and the terminology used will be explained.

In order to characterize pressures and temperatures, the present application uses the terms "pressure level" and "temperature level," which are intended to express the fact that corresponding pressures and temperatures do not need to be used respectively in the form of exact pressure or temperature values in the context of the invention in order to implement the inventive concept. Such pressures and temperatures instead fluctuate typically within specific ranges that can be, for example, 1%, 5%, 10%, 20%, or even 50% above or below an average. Pressure levels in particular, for example, include unavoidable or expected pressure losses, for example as a result of cooling effects. The same is true of temperature levels. The pressures indicated here in kPa are pressures above atmospheric pressure.

A "compound that is capable of pressure- and/or temperature-dependent release of at least one aldehyde" is understood here as a compound that, in a suitable solvent and in coaction with said solvent, in particular in an equilibrium reaction, forms at least one aldehyde as a product. The compound capable of pressure- and/or temperature-dependent release of at least one aldehyde represents the educt of a corresponding equilibrium reaction. Those compounds in which a corresponding equilibrium reaction is located on the side of the educt, i.e. of the compound capable of pressure- and/or temperature-dependent release of at least one aldehyde itself, are used in particular in the context of the present invention. Such a compound always forms the at least one aldehyde in the solvent only in the quantity in which it is withdrawn from the reaction system. As mentioned earlier, corresponding reactions are known in principle for the fixing of tissue samples.

The release is pressure- and/or temperature-dependent when the center point of the aforementioned equilibrium, and/or a reaction rate, can be influenced toward the products or educts by way of a change in pressure and/or temperature. Compounds of interest in the context of the present invention are in particular those for which formation of the at least one aldehyde can be accelerated or increased by way of an elevation in temperature and/or pressure.

As is also further explained below, corresponding nitrogen-containing compounds form in particular by formation of a complex of ammonia and the corresponding at least one aldehyde. These are therefore not pure condensation products and/or hydration products of corresponding aldehydes. In particular, compounds formed by hydration such as methylene glycol, or polymerizates such as paraformaldehyde, are not encompassed thereby.

ADVANTAGES OF THE INVENTION

The present invention proceeds from a method for fixing at least one tissue sample, which method is carried out using a tissue processor and in which method the at least one tissue sample is introduced into a fixing reagent at a first temperature level and at a first pressure level. The fixing reagent contains at least one nitrogen-containing compound capable of pressure- and/or temperature-dependent release of at least one aldehyde, as explained above. As in the case of conventional fixing methods, here as well the at least one tissue sample is left in the fixing reagent at least for a fixing time period.

Provision is now made according to the present invention to bring the fixing reagent having the at least one tissue sample introduced thereinto, during the fixing time period, to a second temperature level above the first temperature level and/or to a second pressure level above the first pressure level. The present invention further provides that a concentration in the fixing reagent of the at least one nitrogen-containing compound capable of pressure- and/or temperature-dependent release of the at least one aldehyde is ascertained using at least one concentration measuring device of the tissue processor, and a signal is outputted on the basis of a measured value of the at least one concentration measuring device.

The essence of the present invention is thus a method in which at least one aldehyde is released in controlled fashion from corresponding donors by the application of pressure and/or temperature. A substantial advantage of the present invention as compared with the existing art is the controllable release of the corresponding aldehyde under controlled conditions, for example inside a closed reaction chamber of a tissue processor. Under the corresponding application of pressure and/or temperature, a corresponding compound releases the at least one aldehyde in amplified fashion. The compound breaks down, for example via one or more intermediates, into the at least one aldehyde and ammonia.

Without the corresponding application of pressure and/or temperature, the at least one aldehyde is not released quantitatively and the molecular structure of the nitrogen-containing compound capable of pressure- and/or temperature-dependent release of the at least one aldehyde is largely stable. A corresponding compound is at best broken down to the extent that the at least one aldehyde is consumed by the at least one tissue sample.

Without the corresponding application of pressure and/or temperature, the fixing speed is therefore relatively slow as compared with conventional formalin solutions as explained previously. A reaction speed or fixing speed corresponding to conventional formalin fixing is achieved only as a result of release due to the application of pressure and/or temperature. This furthermore eliminates a substantial disadvantage of the known existing art in which nitrogen-containing compounds capable of releasing aldehydes are used. In such conventional methods, if fixing is too slow there is a risk of so-called "under-fixing," which can result in autolysis.

As compared with conventional methods for formalin fixing, the method proposed according to the present invention is moreover suitable for appreciably reducing the aforementioned health risk when using aldehyde fixing. When a nitrogen-containing compound capable of releasing formaldehyde is used according to the present invention in the fixing reagent, significant parts of a conventional formalin fixing method can be reproduced by the proposed method. The controlled release of the at least one aldehyde performed according to the present invention is preferably also reversible, i.e. at a lower pressure and lower temperature below the second temperature level and/or below the second pressure level, the nitrogen-containing compound capable of pressure- and/or temperature-dependent release of the at least one aldehyde can form again. The concentration of the free aldehyde decreases due to the shift in the equilibrium reaction. This makes it possible to store a corresponding fixing reagent in a tissue processor and/or in a storage container with no risk to the health of an operator, and to regenerate it economically after fixing.

As mentioned, methylene glycol is a hydration product that releases formaldehyde. In conventional formalin fixing, in which methylene glycol correspondingly forms, formaldehyde is introduced into water directly as a gas. The nitrogen-containing compounds capable of pressure- and/or temperature-dependent release of the at least one aldehyde that are used in the context of the present invention, however, are introduced into water as a salt-like substance, but initially have an extremely small aldehyde-releasing effect, or no such effect. It is only in conjunction with a consumer that aldehyde is released, in particular at a low pH, and forms, for example, methylene glycol in water. Corresponding hydration products are thus produced in secondary fashion. The consequence thereof is that in the context of the present invention advantageously at least two equilibrium reactions (not including reactions of the intermediates) are combined, only the latter ensuring fixing in the manner of conventional formalin.

A nitrogen-containing compound capable of pressure- and/or temperature-dependent release of the at least one aldehyde is therefore split into intermediates and end products only as a result of pressure and temperature. In addition, the increase in temperature and pressure can advantageously promote or influence the actual formalin fixing. Below approx. 20° C., methylene glycol is present without a partial charge. In this form it can permeate through tissue more easily than the charged form. Above 20° C. the charged form is more prevalent. Only in the latter form does a reaction with proteins occur to an appreciable extent.

Homogeneous fixing of the at least one tissue sample is achieved by complete permeation of the at least one tissue sample by the fixing reagent. This permeation can be achieved before or during the application of the requisite pressure and/or requisite temperature of the second pressure level and/or temperature level. It is advantageous here to use maximum times of, for example, one hour, since otherwise autolysis can occur.

The method according to the present invention advantageously enables three-step fixing. The tissue of the at least one tissue sample is firstly entirely or partly permeated. The at least one aldehyde is then released by the application of pressure and/or temperature, and fixing occurs. After fixing, the fixing reagent is removed and, for example, pumped back into a storage container where it is, for example, cooled and/or depressurized and thus once again becomes harmless.

Consumption of the at least one aldehyde causes the fixing reagent to become depleted over time, so that its fixing effect diminishes. In conventional formalin solutions, outgassing of the formaldehyde is moreover observed and/or the formaldehyde becomes oxidized by atmospheric oxygen to formic acid. Outgassing of the formaldehyde furthermore results in a potential hazard to the user. This can also be the case with the nitrogen-containing compounds that release aldehydes in accordance with the invention, but only to a decidedly small extent. The formaldehyde concentration thus continuously decreases even in the absence of a fixing reaction.

Because, in the context of the present invention, only a specific proportion of the at least one nitrogen-containing compound, capable of pressure- and/or temperature-dependent release of the at least one aldehyde, that is contained in the fixing reagent is released in controlled fashion upon fixing, the fixing reagent can particularly advantageously be used repeatedly. It is particularly advantageous to ascertain the concentration of such a compound as provided according to the present invention because this allows a dependable determination as to whether the compound is still present in a sufficient concentration for a further fixing operation. Incorrect fixing, i.e. over-fixing or under-fixing as explained above, can thereby be reliably avoided.

The concentration can be ascertained before, during, or after fixing. In order to furnish a fixing reagent or a component thereof that contains the at least one nitrogen-containing compound capable of pressure- and/or temperature-dependent release of the at least one aldehyde it is possible, for example, to use reservoir containers (cartridges or retorts) specifically adapted to the tissue processor, which comprise unequivocal identification features. Such reservoir containers, in which corresponding identification features can also be embodied in mishandling-proof fashion (for example by using encrypted codes in RFID or NFD chips or barcodes), are introduced into the tissue processor. In the tissue processor it is possible to ascertain, on the basis of the identification features, whether a corresponding concentration has already been ascertained once in that reservoir container. If so, the tissue processor "knows" whether the fixing reagent is still suitable for further fixing. When a corresponding container is used for the first time, an unequivocal assignment of that container to a specific tissue processor can also be effected, so that it is no longer possible to use the container in another tissue processor. Intentional or unintentional mishandling or incorrect operation can thus be avoided, and reliable fixing guaranteed.

A corresponding container can also, for example, comprise memory means, for example in the form of writable memory chips, which allow the concentration, ascertained by a tissue processor, of the at least one compound capable of pressure- and/or temperature-dependent release of the at least one aldehyde to be stored. The tissue processor can ascertain this concentration, for example, at the end of a fixing operation, and store it in the memory means of the container. A corresponding container can thus also be used in another tissue processor that is in turn capable of reading out the memory means.

Ascertaining the concentration of the at least one nitrogen-containing compound capable of pressure- and/or temperature-dependent release of the at least one aldehyde is also advantageous in particular because as a function of the concentration that is ascertained, for example a fixing time and/or the pressure used in the fixing operation according to the present invention and/or the temperature used in the fixing operation according to the present invention can be adapted thereto. For example, after repeated use of the fixing reagent the concentration of a corresponding compound can decrease in such a way that a longer fixing time and/or a change in corresponding pressure and/or temperature values is necessary. If the concentration is ascertained before a fixing operation or if, as explained, it is known, for example, from a previous fixing operation (e.g. associated with a reservoir container or stored in memory means of a corresponding reservoir container), a corresponding adaptation can be made particularly simply.

During fixing, ascertaining the concentration of the at least one nitrogen-containing compound capable of pressure- and/or temperature-dependent release of the at least one aldehyde is advantageous in particular because by way of the compound consumed in each case, it is possible to infer the success of the fixing operation itself. For example, fixing can be carried out until a decrease in concentration by a predefined value is observed. This allows the inference that a specific quantity of the at least one aldehyde has been released and has thus at least in part traveled into the sample to be fixed.

A corresponding tissue processor can operate in the context of the present invention with threshold values that are permanently defined in mishandling-proof fashion or with ones that are predefinable. Provision can be made, for example, that when the concentration of the at least one nitrogen-containing compound capable of pressure- and/or temperature-dependent release of the at least one aldehyde is below such a threshold value, the tissue processor no longer performs fixing and the user is thereby encouraged to exchange the fixing reagent or the corresponding component.

The tissue processor can also be configured to inform a user on the basis of the signal outputted according to the present invention, for example on an output unit such as a monitor, so that the user, for example, always knows the concentration that is present and/or the time and/or the number of fixing operations for which the fixing reagent is still sufficient.

It is proposed in the context of the invention to use room temperature (i.e. for example a temperature from 20 to 25° C.) and/or a cold-storage temperature (i.e. for example 0 to 10° C. or −25 to −15° C.) as the first temperature level, and to use a temperature above corresponding temperatures, in particular above room temperature, for example a temperature from 20 to 80° C., as the second temperature level. Thanks to the use of corresponding temperature levels that are respectively adapted to the nitrogen-containing compound capable of pressure- and/or temperature-dependent release of at least one aldehyde or vice versa, a corresponding fixing reagent can be handled safely.

The same is also true of the pressure levels advantageously used according to the present invention. For example, the first pressure level is in particular atmospheric pressure or even lower, the latter for example for vacuum infiltration of a tissue sample; and the second pressure level corresponds to an above-atmospheric pressure level. For example, 5 to 1000 kPa gauge pressure, for example 5 to 20, 20 to 50, 50 to 100, 100 to 500, or 500 to 1000 kPa gauge pressure, can be used as an above-atmospheric pressure level. At elevated temperatures and pressures, the chemical equilibrium for the nitrogen-containing compounds used in the context of the present invention and capable of pressure- and/or temperature-dependent release of the at least one aldehyde is on the side of the respective aldehyde.

Reaction products of ammonia and the at least one aldehyde are used in particular in the context of the present invention as nitrogen-containing compounds capable of pressure- and/or temperature-dependent release of at least one aldehyde. The at least one aldehyde is formaldehyde and/or glutaraldehyde, or other aldehydes. Compounds such as urotropin, triazines, dimethyloldihydroxyethylene urea, mono-, di-, tri-, tetra-, penta-, and hexamethylolmelamine, tetramethylolacetylene diurea, dimethylolpropylene urea, acetoguanamine, and/or 5,5-dimethylhydantoin are particularly suitable for a method as proposed in the context of the present invention. These are so-called formaldehyde releasers.

Formaldehyde release will be illustrated below using the example of urotropin (hexamethylenetetramine), but it is applicable correspondingly to the further compounds. At higher temperatures, the chemical equilibrium in the equation presented below is on the formaldehyde+ammonia side (to the left of the reaction arrow). The result of this is that urotropin (to the right of the reaction arrow) breaks down with the formation of intermediates, and is consumed.

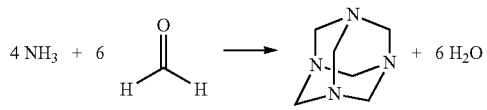

Formaldehyde release is promoted in a weakly acidic aqueous solution at a pH of approximately 3. Various carboxylic acids, for example citric acid, acetic acid, and oxalic acid, but also mineral acids such as boric acid and phosphoric acid, promote the release of formaldehyde.

A comparatively low acid strength, i.e. a pKs value below 6.4, is important for preserving the tissue of a tissue sample being fixed. Acids of this kind additionally accelerate fixing. A suitable pH can be in a range from 2 to 4.

In order to assist infiltration of a corresponding tissue sample, it is advantageous to use a fixing reagent that contains 5 to 50% of at least one alcohol, for example ethanol. Utilization of an alcohol reduces the surface tension of the fixing reagent and its viscosity.

It is particularly advantageous in the context of the present invention if the method explained above is carried out using a tissue processor, the fixing reagent having the at least one tissue sample introduced thereinto being introduced at least intermittently during the fixing time period into a processing chamber of the tissue processor and being brought therein to the second temperature level and/or to the second pressure level. As explained, the use of a tissue processor permits fixing in a closed-off space and thereby avoids risk to personnel.

The explanations above apply in the same manner to the tissue processor proposed according to the present invention, which encompasses at least one process chamber that is configured to receive a sample container having at least one tissue sample introduced into a fixing reagent, the fixing reagent containing, as repeatedly explained, at least one nitrogen-containing compound capable of pressure- and/or temperature-dependent release of at least one aldehyde. A tissue processor of this kind is equipped according to the present invention with means that make it capable of carrying out a method as explained previously. The tissue processor contains at least one concentration measuring device that is configured to ascertain a concentration in the fixing reagent of the at least one nitrogen-containing compound capable of pressure- and/or temperature-dependent release of the at least one aldehyde, and on that basis to output a corresponding signal.

The invention is schematically depicted below in the drawings on the basis of an exemplifying embodiment and will be described in detail below with reference to the drawings.

BRIEF DESCRIPTION OF THE DRAWING FIGURES

DETAILED DESCRIPTION OF THE INVENTION

Figure 1:
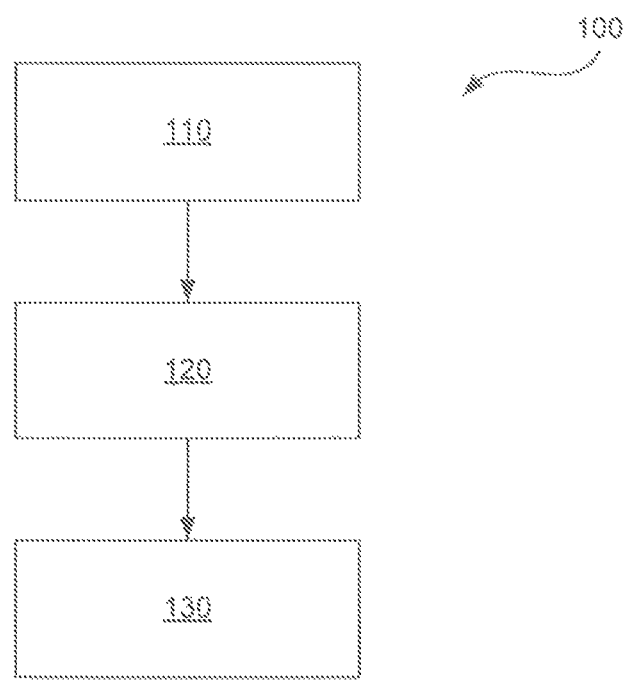
FIG. 1 illustrates a method in accordance with an embodiment of the invention, in the form of a simplified schematic flow chart.

In FIG. 1 a method in accordance with an embodiment of the invention is depicted in the form of a schematic flow chart and labeled 100 in its entirety. As explained before, the method is carried out in the form of a three-step fixing operation and encompasses steps 110, 120, and 130.

In step 110 at least one tissue sample is introduced into a fixing reagent, as repeatedly explained previously. In step 110, advantageously an infiltration of the at least one tissue sample with the fixing reagent may be carried out, for example by vacuum infiltration. Already in step 110, the tissue sample in the fixing reagent in a suitable container can be introduced into a tissue processor. In step 110 the at least one tissue sample is at a first temperature level and a first pressure level in the fixing reagent.

In a step 120 that follows step 110, the at least one tissue sample is left in the fixing reagent at least for a fixing time period. In step 120 the fixing reagent having the at least one tissue sample introduced thereinto is in particular brought during the aforesaid fixing time period, for example in a fixing chamber of a tissue processor, to a second temperature level above the first temperature level and/or to a second pressure level above the first pressure level. The actual fixing of the tissue sample on the basis of the reaction principles previously explained therefore occurs in step 120.

In a step 130 that follows step 120, fixing is terminated. The previously established second temperature level and/or the previously established second pressure level are decreased, for example to the first temperature level and/or pressure level that is present in step 110. Release of the at least one aldehyde from the fixing reagent, and from the nitrogen-containing compound capable of pressure- and/or temperature-dependent release of at least one aldehyde contained therein, is thus terminated. In step 130 any gaseous aldehyde that may be present can be extracted from a fixing chamber of a tissue processor that is being used in method 100. The fixing reagent, in which no further release of the at least one aldehyde is now occurring to an appreciable extent, can now be pumped off and, for example, transferred into a reservoir tank.

Before, during, and/or after the aforesaid steps, a concentration in the fixing reagent of the at least one nitrogen-containing compound capable of pressure- and/or temperature-dependent release of the at least one aldehyde can be ascertained using at least one concentration measuring device of a tissue processor that is used, and a signal can be outputted on the basis of a measured value of the at least one concentration measuring device.

Figure 2:
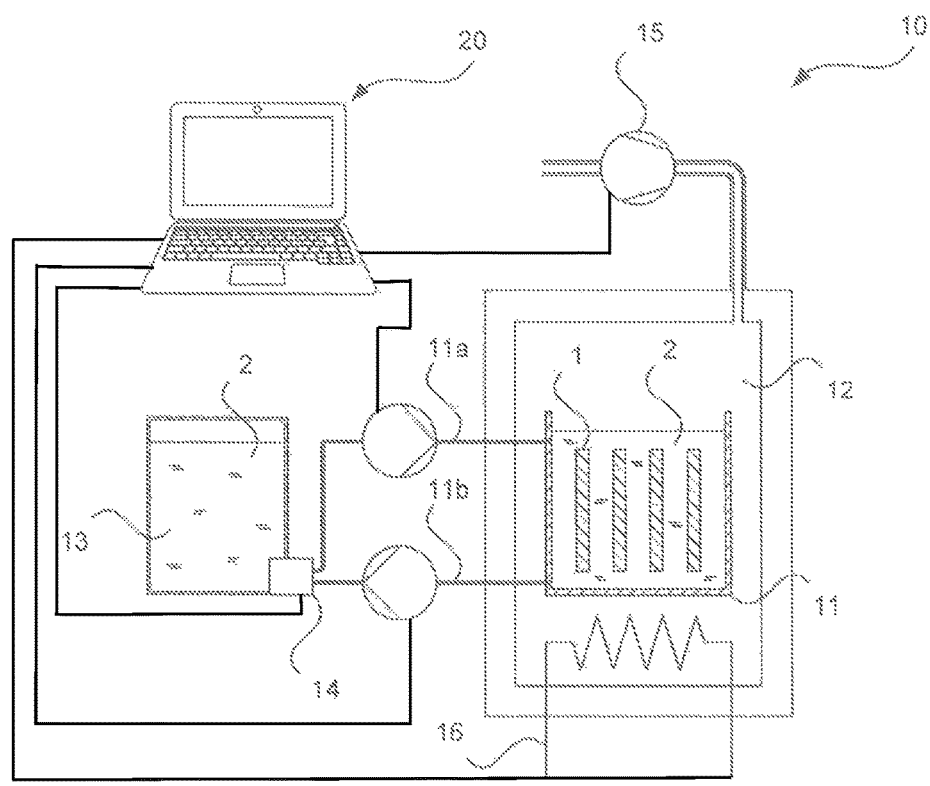
FIG. 2 illustrates a tissue processor in accordance with an embodiment of the invention, in a simplified schematic depiction.

In FIG. 2 a tissue processor in accordance with an embodiment of the invention is schematically depicted and labeled 10. In the example depicted, tissue processor 10 encompasses a sample container 11 in which, as depicted in FIG. 2, four tissue samples 1 (labeled only in part) are introduced into a fixing reagent 2. Suitable fluid lines 11a and 11b having pumps (respectively unlabeled) are provided for the introduction and removal of fixing reagent into and from sample container 11. Lines 11a and 11b are connected to a reservoir container 13.

Associated with reservoir container 13 is a concentration measuring device 14 that is configured to ascertain, for example using spectrophotometric methods, a concentration in fixing reagent 2 of the at least one nitrogen-containing compound capable of pressure- and/or temperature-dependent release of the at least one aldehyde. By means of concentration measuring device 14 a signal can be outputted, for example, to a user interface 20 that is configured to operate tissue processor 10. User interface 20 may include a keypad and a screen.

Tissue processor 10 comprises a process chamber 12 into which sample container 11 can be introduced. Process chamber 12 can advantageously be closed off in such a way that no hazard to a user is possible during the repeatedly mentioned fixing time period in which at least one aldehyde may possibly be released. Process chamber 12 can also be connected to an aspiration device (not shown).

Tissue processor 10 furthermore encompasses means 15 and 16 that are configured for the application of pressure and/or temperature to process chamber 12, for example a pressure pump 15 and a heating coil 16.

What is claimed is:

1. A tissue processor (10) comprising:
   at least one process chamber (12) configured to receive a sample container (11) having at least one tissue sample (1) introduced into a fixing reagent (2), the fixing reagent (2) containing at least one nitrogen-containing compound capable of pressure- and/or temperature-dependent release of at least one aldehyde, wherein the at least one nitrogen-containing compound capable of pressure-and/or temperature-dependent release of at least one aldehyde includes urotropin, at least one triazine, dimethyloldihydroxyethylene urea, mono-, di, tri-, tetra-, penta-, and hexamethylolmelamine, tetramethylolacetylene diurea, dimethylolpropylene urea, acetoguanamine, and/or 5,5-dimethylhydantoin;
   a reservoir container (13) in fluid communication with the sample container (11), the reservoir container storing fixing reagent (2);
   a concentration measuring device (14) associated with the reservoir container (13), wherein the concentration measuring device (14) is configured to ascertain a concentration in fixing reagent (2) of the at least one nitrogen-containing compound capable of pressure- and/or temperature-dependent release of the at least one aldehyde; and
   a control system operatively connected to the concentration measuring device, wherein the control system is programmed to operate the tissue processor (10), and wherein the tissue processor modifies at least one of a fixing time, a pressure, and a temperature of a fixing operation based on the concentration ascertained by the concentration measuring device;
   wherein the tissue processor (10) further comprises at least one of:
      a pressure pump in fluid communication with the at least one process chamber (12) for increasing pressure within the at least one process chamber (12), wherein the pressure pump is operatively connected to the control system; and
      a heating coil within the at least one process chamber (12), wherein the heating coil is operatively connected to the control system.

2. The tissue processor (10) according to claim 1, wherein the concentration measuring device (14) includes a spectrophotometric concentration measuring device.

3. The tissue processor (10) according to claim 1, wherein the control system further comprises a keypad and screen, and wherein the concentration measuring device (14) outputs a measured value signal to the screen.

* * * * *